US010189945B2

(12) United States Patent
Sanders et al.

(10) Patent No.: US 10,189,945 B2
(45) Date of Patent: Jan. 29, 2019

(54) METHOD FOR PRODUCING LIGHT-COLOURED TDI-POLYISOCYANATES

(71) Applicant: Covestro Deutschland AG, Leverkusen (DE)

(72) Inventors: Josef Sanders, Leverkusen (DE); Andreas Hecking, Langenfeld (DE); Reinhard Halpaap, Odenthal (DE); Frank Richter, Leverkusen (DE); Oswald Wilmes, Cologne (DE); Jan Busch, Dusseldorf (DE); Tim Loddenkemper, Dormagen (DE); Friedhelm Steffens, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 90 days.

(21) Appl. No.: 14/774,297

(22) PCT Filed: Mar. 7, 2014

(86) PCT No.: PCT/EP2014/054423
§ 371 (c)(1),
(2) Date: Sep. 10, 2015

(87) PCT Pub. No.: WO2014/139873
PCT Pub. Date: Sep. 18, 2014

(65) Prior Publication Data
US 2016/0017097 A1 Jan. 21, 2016

(30) Foreign Application Priority Data
Mar. 12, 2013 (EP) .................................... 13158689

(51) Int. Cl.
C08G 18/00 (2006.01)
C08G 71/04 (2006.01)
C07C 269/02 (2006.01)
C08G 18/76 (2006.01)
C08G 18/78 (2006.01)
C09D 175/04 (2006.01)
C08G 18/32 (2006.01)
C08G 18/42 (2006.01)
C09J 175/04 (2006.01)

(52) U.S. Cl.
CPC ............ C08G 71/04 (2013.01); C07C 269/02 (2013.01); C08G 18/3206 (2013.01); C08G 18/42 (2013.01); C08G 18/7621 (2013.01); C08G 18/7843 (2013.01); C09D 175/04 (2013.01); C09J 175/04 (2013.01)

(58) Field of Classification Search
CPC ................ C08G 18/3206; C08G 18/42; C08G 18/7621; C08G 18/7843; C08G 71/04; C09D 175/04; C09J 175/04; C07C 269/02
See application file for complete search history.

(56) References Cited

U.S. PATENT DOCUMENTS

| 3,183,112 | A | | 5/1965 | Gemassmer | |
|---|---|---|---|---|---|
| 3,839,491 | A | * | 10/1974 | Gamero | C08G 18/10 528/59 |
| 4,910,332 | A | * | 3/1990 | Kahl | C07C 271/28 560/351 |
| 5,468,804 | A | | 11/1995 | Schmalstieg et al. | |
| 5,747,628 | A | | 5/1998 | Schmalstieg et al. | |
| 5,872,278 | A | | 2/1999 | Kraus et al. | |
| 6,391,161 | B1 | * | 5/2002 | Danielmeier | C07C 263/20 203/100 |
| 6,395,925 | B1 | * | 5/2002 | Danielmeier | C07C 263/20 560/330 |
| 6,900,348 | B1 | | 5/2005 | Reif et al. | |
| 2010/0249450 | A1 | * | 9/2010 | Maeba | B01D 3/14 560/352 |

FOREIGN PATENT DOCUMENTS

| CA | 2209139 A1 | 12/1997 |
|---|---|---|
| DE | 870 400 C | 3/1953 |
| DE | 953 012 C | 11/1956 |
| DE | 1 090 186 B | 10/1960 |
| DE | 1090196 B | 10/1960 |
| EP | 0546399 A2 | 6/1993 |
| EP | 0 816 333 A1 | 1/1998 |
| EP | 0 866 057 A2 | 9/1998 |
| EP | 1 187 808 A1 | 3/2002 |
| EP | 1413571 A1 | 4/2004 |
| EP | 1 864 969 A1 | 12/2007 |
| WO | WO-0100569 A1 | 1/2001 |

OTHER PUBLICATIONS

International Search Report for PCT/EP2014/054423 dated May 20, 2014.
Paint and Coating Testing Manual, Fourteenth Edition of the Gardner-Sward Handbook, Josef V. Koleske, ASTM Manual Series MNL 17, ASTM Publication Code No. (PCN) 28-017095-14, pp. 115-116.
Gordon, Measure True Color, What is the Relationship between the APHA/Pt-Co/Hazen and Gardner, Oct. 22, 2012, pp. 1-2.
ASTM International, Designation: D 4663-98, Standard Test Method for Polyurethane Raw Materials: Determination of Hydrolyzable Chlorine of Isocyanates 1, pp. 1-2.
ASTM International, Designation D 4661-03, Standard Test Methods for Polyurethane Raw Materials: Determination of Total Chlorine in Isocyanates 1, pp. 1-2.

* cited by examiner

Primary Examiner — Michael L Leonard
(74) Attorney, Agent, or Firm — John E. Mrozinski, Jr.

(57) ABSTRACT

The invention relates to polyisocyanates comprising urethane groups, based on toluylene diisocyanate, to a method for their production, and to their use as the polyisocyanate component in one- and two-component polyurethane coatings.

11 Claims, No Drawings

METHOD FOR PRODUCING LIGHT-COLOURED TDI-POLYISOCYANATES

CROSS-REFERENCE TO RELATED APPLICATIONS

This application is a national stage application (under 35 U.S.C. § 371) of PCT/EP2014/054423, filed Mar. 7, 2014, which claims benefit of European Application No. 13158689.3, filed Mar. 12, 2013, both of which are incorporated herein by reference in their entirety.

The invention relates to polyisocyanates comprising urethane groups, based on toluylene diisocyanate, to a method for their production, and to their use as the polyisocyanate component in one- and two-component polyurethane coatings.

Polyisocyanates comprising urethane groups and based on low molecular weight polyhydroxy compounds and toluylene diisocyanate (TDI) have been known for a long time and are described, for example, in German patent specifications DE 870 400, 953 012 and DE 1 090 196. Such products are of great importance in the field of polyurethane coatings, in particular in the coating of wood, and in the adhesives sector. Commercial products are nowadays produced by reacting polyhydroxy compounds with the 5- to 10-times molar amount of toluylene diisocyanate, followed by removal of excess starting diisocyanate by distillation, preferably in a thin-film evaporator. Such methods are described, for example, in DE-PS 1 090 186 or U.S. Pat. No. 3,183,112. In EP 0 546 399, polyisocyanates comprising ether and urethane groups and based on polyhydroxy polyethers and toluylene diisocyanate having a content of free TDI of <0.1% are claimed. However, the polyisocyanates of the prior art produced in that manner have the fundamental disadvantage that, like most aromatic polyisocyanates, they have a significantly higher intrinsic colour in comparison with aliphatic coating polyisocyanates. On account of this intrinsic colour, they can be used to only a limited extent in particular for the coating of lighter wood types which have recently been in greater demand, because the parts coated therewith appear darker and their grain, which even before coating is only subtle, is scarcely discernible after coating.

Both the intrinsic colour of the TDI used and an insufficient purity of light-coloured TDI frequently lead to discoloured polyisocyanates. There has therefore been no lack of attempts to prepare TDI grades with which lighter-coloured aromatic polyisocyanates can be produced. For example, EP 1 413 571 describes a process with which a product fraction having a TDI content of at least 99.5% and less than 200 wt·ppm solvent and/or chlorinated aromatic hydrocarbons, less than 100 wt·ppm hydrolysable chlorine and less than 40 wt·ppm acid is obtained by preconcentrating the crude TDI solution to a solids content of <20%, followed by fractionation in a dividing wall distillation column. In U.S. Pat. No. 6,900,348, or in the corresponding EP 1 187 808, it is described that lighter-coloured diphenylmethane diisocyanates can be obtained by using phosgene having a bromine content of <50 ppm. EP 0 816 333 claims a method for reducing the colour of TDI by treating the crude solution with hydrogen before the solvent is separated off.

Special pretreatment of the toluylenediamine (TDA) used to produce TDI can also lead to a reduction of the TDI colour. For example, EP 1 864 969 claims a method for producing lighter-coloured TDI in which the TDA used therefor in the phosgenation comprises less than 0.1 wt. % alkylated cyclic ketones, based on 100 wt. % TDA. In U.S. Pat. No. 5,872,278 or the corresponding EP 0 866 057, a method is described in which the amine used is treated with solids containing Lewis and/or Brönstedt acid centres before the reaction with phosgene. The isocyanates obtained then have a lighter colour than isocyanates produced using untreated amine.

Although these comparatively very complex methods permit the production of TDI grades with greater purity and a lighter colour, there is no indication therein of which secondary components are responsible for the still insufficiently preventable discolouration of the polyisocyanates during their production and how this discolouration can be prevented to a sufficient degree. There is therefore still an urgent need for light-coloured aromatic coating polyisocyanates.

The object of the present invention was to find a method with which light-coloured polyisocyanates comprising urethane groups, based on toluylene diisocyanate can be produced.

It has been possible to achieve that object with the method described in greater detail below.

The invention is based on the surprising observation that light-coloured polyisocyanates based on toluylene diisocyanate can be produced by reacting low molecular weight polyhydroxy compounds with from 5- to 10-times the amount of TDI and then removing excess TDI preferably by thin-film distillation in vacuo, wherein the TDI used has a content of 2-chloro-6-isocyanato-methylcyclohexadienes (CIMCH) of <5 wt·ppm. Light-coloured in this context means that the polyisocyanates so produced have APHA colour indices of <50 Hazen, preferably <30 Hazen, particularly preferably ≤25 Hazen, measured on the basis of DIN EN 1557.

CIMCH can be in the form of 3 double bond isomers which can be present in the TDI in different ratios. These are formed, for example, in TDI production from 1-amino-2-methyl-cyclohexenone contained in the TDA used, which in turn can form in the production of TDA from dinitrotoluene (DNT) by partial nuclear hydrogenation of TDA and replacement of an amino functional group by water. It is also possible that the keto functional group is already introduced proportionately by oxidative attack in the production of DNT by nitration of toluene, there first being formed nitrocresols which can then form the above-described 1-amino-methyl-2-cyclohexenone in the subsequent hydrogenation.

Accordingly, the invention provides a method for producing light-coloured polyisocyanates having APHA colour indices<50 Hazen by reacting organic polyhydroxy compounds with excess amounts of toluylene diisocyanate and then removing unreacted toluylene diisocyanate by distillation, characterised in that the toluylene diisocyanate used has a content of 2-chloro-6-isocyanato-methylcyclohexadienes (CIMCH) of <5 wt·ppm.

The invention also provides the light-coloured polyisocyanates having APHA colour indices <50 Hazen which are obtainable by the method according to the invention, and their use as the polyisocyanate component in polyurethane coatings, in particular in two-component polyurethane coatings.

Starting materials for the method according to the invention are toluylene diisocyanate and low molecular weight polyhydroxy compounds.

There come into consideration as the toluylene diisocyanate in particular 2,4-toluylene diisocyanate and commercial mixtures thereof with up to 35 wt. %, based on the mixture, of 2,6-toluylene diisocyanate, which have a content of 2-chloro-6-isocyanato-methylcyclohexadienes (CIMCH) of <5 wt·ppm, preferably of ≤3 wt·ppm. Such TDI grades can be obtained, for example, by purposive removal of 2-chloro-6-isocyanato-methylcyclohexadienes from the preconcentrated crude TDI solutions by distillation by means of a dividing wall distillation column, as is described in EP 1 413 571 B1. Particular preference is given, however, to toluylene diisocyanates which are produced by gas phase phosgenation of TDA and whose content of 2-chloro-6-isocyanato-methylcyclohexadienes is below the detection limit. Toluylene diisocyanate of such a grade is obtainable, for example, from Bayer Material Science AG from the production at the Caojing site in China.

Two independent analytical methods have been used for the clear characterisation of the component 2-chloro-6-isocyanato-methylcyclohexadienes. By means of gas chromatography techniques, different toluylene diisocyanate grades having a 2,4 content of about 80 wt. % were tested for their dissimilarities in the secondary component spectrum. By subsequent coupled gas chromatography-mass spectroscopy, a molecular weight of 169 g/mol was allocated to the three hitherto unknown compounds (CIMCH including two isomers). It was possible to obtain further structural information from the fragmentation in a manner known to the person skilled in the art. By means of complex nuclear resonance spectroscopy experiments ($^1$H-NMR, $^1$H-COSY, $^1$H-,$^1$H-TOCSY and $^1$H-,$^{13}$C-HMBC), the structures indicated below could be allocated to the three components with m/z 169.

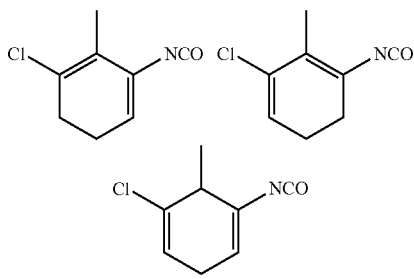

By purposive method development it was possible to set the detection limit of the isomers of CIMCH by means of gas chromatography-spectroscopy, using an Optima 5 HT column (60 m length, 0.25 mm inside diameter, 0.25 μm film thickness) from Macherey-Nagel in an HP Series 6890 gas chromatograph from Hewlett Packard, at 1 wt·ppm.

As low molecular weight polyhydroxy compounds which are to be used in the method according to the invention there are used di- to tetra-hydric alcohols having a molecular weight of from 62 to 146 and/or polyether polyols prepared therefrom by addition of ethylene oxide and/or propylene oxide, in pure form or in the form of arbitrary mixtures.

There come into consideration as di- to tetra-hydric alcohols, for example, ethylene glycol, 1,2-propylene glycol, 1,3-propylene glycol, 1,2-butanediol, 1,3-butanediol, 1,4-butanediol, 1,5-pentanediol, neopentyl glycol, 1,6-hexanediol, 2-ethylhexanediol, glycerol, trimethylolpropane and pentaerythritol.

Suitable polyether polyols have a molecular weight, calculable from the hydroxyl group content and hydroxyl functionality, of from 106 to 600, preferably from 106 to 470. Polyether diols and polyether triols are preferably used. These polyether polyols can be obtained in a manner known per se by alkoxylation of suitable di- to tetra-functional starter molecules or suitable mixtures of starter molecules, there being used in the alkoxylation in particular propylene oxide and/or ethylene oxide, optionally in a mixture in succession in any desired sequence. The above-mentioned di- to tetra-hydric alcohols are preferably used as starter molecules. Mixtures of trimethylolpropane and diethylene glycol are most particularly preferably used.

In order to carry out the method according to the invention, the polyhydroxy compounds are reacted with toluylene diisocyanate at temperatures of from 40 to 140° C., preferably from 70 to 110° C. The amounts of the reactants generally correspond to an NCO/OH equivalent ratio of from 4:1 to 20:1, preferably from 5:1 to 10:1.

After the prepolymerisation, excess unreacted toluylene diisocyanate is removed by vacuum thin-film distillation at from 100 to 180° C., preferably from 120 to 160° C. The polyisocyanates according to the invention are thereby obtained in the form of hard to semi-hard resins.

The polyisocyanates produced by the method according to the invention are polyisocyanate mixtures, analysis of which by gel chromatography shows the simultaneous presence of a plurality of polyisocyanate components, the composition and functionality of which depend on the hydroxy compounds used and the TDI excess present in the prepolymerisation. The main products are in each case the "monomeric" urethanes which have formed by reaction of the individual hydroxy compounds with the number of TDI molecules corresponding to their functionality. However, oligomeric urethanes with higher molecular weights, which can comprise two or more polyhydroxy molecules, are additionally also present, the relative proportion of the higher molecular weight oligomers falling as the TDI excess in the prepolymerisation increases. The functionalities of the main components correspond to those of the polyhydroxy components used and are accordingly two, three or four, while the oligomers present as secondary components in each case have higher functionalities. The mean functionality of the products produced by the method according to the invention, which can be calculated from the isocyanate content and the molecular weight determined by gel chromatography, is from 2.0 to 4.0, preferably from 2.5 to 3.5, most particularly preferably from 2.8 to 3.2. Determinations by gel chromatography were carried out using a gel chromatograph of the HP 1100 type from Hewlett Packard. To that end there was used a 4-fold column assembly from Macherey & Nagel (2 Nucleogel-100 and 2 Nucleogel-50 plus a Nucleogel-10 precolumn) at 35° C. using a polystyrene standard and THF as eluant.

The polyisocyanates produced according to the invention are generally used in the form of a solution in an organic solvent. Suitable solvents are, for example, the known coating solvents such as ethyl acetate, butyl acetate, methoxypropyl acetate, toluene, the isomeric xylenes, and commercial solvents such as ®Solvent Naphtha or ®Solvesso or mixtures of such solvents.

The polyisocyanates produced by the method according to the invention are valuable raw materials for one- and two-component polyurethane coatings. The particularly preferred field of use for these polyisocyanates is their use as the polyisocyanate component in two-component polyurethane coatings. The reactants for the polyisocyanates according to the invention that are preferred for this preferred use are the polyhydroxy polyesters and polyethers, polyhydroxy polyacrylates and optionally low molecular weight polyhydric alcohols which are known per se in polyurethane coating technology.

Polyamines, in particular in blocked form as polyketimines or oxazolidines, are also conceivable reactants for the method according to the invention. The ratios in which the polyisocyanates produced by the method according to the invention and the mentioned reactants are used in the production of two-component polyurethane coatings are generally so chosen that there are from 0.8 to 3.0, preferably from 0.9 to 1.1, groups reactive towards isocyanate groups per isocyanate group.

Depending on the choice of polyhydroxy components used, the two-component polyurethane coating compositions can have different pot lives. If particularly rapid curing is desired, the catalysts conventional in isocyanate chemistry, such as, for example, amines such as triethylamine, pyridine, methylpyridine, benzyldimethylamine, N,N'-dimethylpiperazine or metal salts such as iron(III) chloride, zinc chloride, zinc 2-ethylcaproate, tin(II) 2-ethylcaproate, dibutyltin(IV) dilaurate or molybdenum glycolate, can be used concomitantly.

One-component polyurethane coatings which comprise polyisocyanates produced by the method according to the invention as binders, and in particular two-component polyurethane coatings which comprise polyisocyanates produced by the method according to the invention as crosslinkers, lead to hard but still resilient coating films which have high abrasion resistance with excellent adhesion to a very wide variety of substrates. In addition, the coating films are distinguished by their very low discolouration, so that even the grain of light wood types coated therewith can clearly be seen.

The polyurethane coatings which comprise polyisocyanates produced by the method according to the invention as binders or as curing agents can naturally comprise auxiliary substances and additives conventional in coating technology, such as pigments, flow aids, fillers and the like.

EXAMPLES

In the examples which follow, all percentages are by weight. The following methods were used to characterise the products obtained:

The NCO content of the resins described in the examples and comparative examples was determined by titration according to DIN EN ISO 11 909.

The dynamic viscosities were measured according to DIN 3219 with a DIN measurement body 125 at 23° C. using a Reolab QC viscometer from Anton Paar in the shear rate range of from 1 to 1600 l/s.

The residual monomer contents were determined by gas chromatography according to DIN EN ISO 10283.

The solids content (non-vaporisable portion) was determined according to DIN 3251 under the test conditions described therein for isocyanates.

The colour indices were measured at 23° C. on the basis of DIN EN 1557 using a LICO 400 from HACH Lange in 50 mm disposable rectangular cuvettes.

Example 1 (In Accordance with the Invention)

660 g of toluylene diisocyanate having a 2,4 content of about 80 wt. % and a content of CIMCH of 3 wt·ppm are placed in a 1000 ml double-jacketed ground glass vessel. The reaction vessel is heated to the desired reaction temperature of 85° C. Then, within a period of 30 minutes, 80 g of the polyol mixture, preheated to 65° C., comprising a mixture of trimethylolpropane and diethylene glycol is metered in continuously. The heat of reaction thereby liberated is dissipated safely by means of a refrigerated-heating circulator, so that the procedure can be referred to as isothermal. The crude solution comprising urethane groups is then stirred for a further 45 minutes at the given temperature. The determination of the NCO content which is subsequently carried out gives 33.4 wt. %, which corresponds to the theoretical value. The viscous colourless solution obtained is freed of excess monomeric toluylene diisocyanate by two-stage vacuum thin-film distillation (145° C./155° C.; p≤0.5 mbar) in the course of 90 minutes. While still warm, the polyisocyanate comprising urethane groups present in an amount of 290 g is dissolved to 75 wt. % in ethyl acetate. The polyisocyanate comprising solvent and urethane groups so obtained has the following characteristic values:
NCO content=13.27 wt. %
Viscosity=1490 mPa*s @23° C.
Residual monomer content=0.29 wt. %
Solids content=75.2 wt. %
APHA colour index=25 Hazen Example 2 (In Accordance with the Invention)

The procedure is analogous to Example 1, but the reaction is carried out with toluylene diisocyanate having a 2,4 content of about 80 wt. % which was produced by gas phase phosgenation, and a content of CIMCH below the detection limit (<1 wt·ppm). The polyisocyanate comprising solvent and urethane groups so obtained has the following characteristic values:
NCO content=13.24 wt. %
Viscosity=1505 mPa*s @23° C.
Residual monomer content=0.25 wt. %
Solids content=74.9 wt. %
APHA colour index=21 Hazen Example 3 (Not in Accordance with the Invention)

The procedure is analogous to Example 1, but the reaction is carried out with toluylene diisocyanate having a 2,4 content of about 80 wt. % which has a content of CIMCH of 160 wt·ppm. The polyisocyanate comprising solvent and urethane groups so obtained has the following characteristic values:
NCO content=13.23 wt. %
Viscosity=1510 mPa*s @23° C.
Residual monomer content=0.26 wt. %
Solids content=75.3 wt. %
APHA colour index=80 Hazen Example 4 (Not in Accordance with the Invention)

The procedure is analogous to Example 1, but the reaction is carried out with toluylene diisocyanate having a 2,4 content of about 80 wt. % which has a content of CIMCH of 70 wt·ppm. The polyisocyanate comprising solvent and urethane groups so obtained has the following characteristic values:
NCO content=13.28 wt. %
Viscosity=1500 mPa*s @23° C.
Residual monomer content=0.27 wt. %
Solids content=75.0 wt. %
APHA colour index=62 Hazen Example 5 (Not in Accordance with the Invention)

The procedure is analogous to Example 1, but the reaction is carried out with toluylene diisocyanate having a 2,4 content of about 80 wt. % which has a content of CIMCH of 35 wt·ppm. The polyisocyanate comprising urethane groups so obtained has the following characteristic values:

NCO content=13.24 wt. %
Viscosity=1480 mPa*s @23° C.
Residual monomer content=0.28 wt. %
Solids content=75.3 wt. %
APHA colour index=55 Hazen Examples 1 to 5 show that when toluylene diisocyanate having CIMCH contents <5 wt·ppm are used, light-coloured polyisocyanates having APHA colour indices <50 Hazen are obtained.

Example 6, Use

The polyisocyanates from Example 1 and Example 3 are each mixed in the NCO/OH ratio 1:1 with a commercially available polyester polyol (®Desmophen 1300, commercial product from Bayer AG, hydroxyl content 4 wt. %) to give a total concentration of 40 wt. % in butyl acetate. The use-specific comparison shows no differences at all in the coating-related properties.

|  |  |  | Example 1 | Example 3 |
|---|---|---|---|---|
| Formulation Sample preparation according to DIN EN ISO 1513 and subsequent conditioning according to ISO 3270 | Amount Desmodur | [g] | 25.9 | 25.9 |
|  | Type | | 13001X | 13001X |
|  | Amount Desmophen | [g] | 43.5 | 43.5 |
|  | Solvent | | Butyl acetate | Butyl acetate |
|  | Amount Solvent | [g] | 60.7 | 60.7 |
|  | Solids content | [%] | 40 | 40 |
|  | NCO/OH ratio | | 1.0 | 1.0 |
| Flow time according to DIN 53211 in a 4 mm cup | 0 h | [m'ss"hh] | 11"87 | 11"94 |
|  | 8 h | [m'ss"hh] | 12"65 | 12"62 |
|  | 24 h | [m'ss"hh] | 13"78 | 13"66 |
|  | 27 h | [m'ss"hh] | 14"00 | 14"97 |
|  | 30 h | [m'ss"hh] | 14"72 | 15"25 |
|  | 48 h | [m'ss"hh] | 19"69 | 19"06 |
|  | Temperature | [° C.] | 24.8 | 24.8 |
|  | Humidity | [%] | 72 | 72 |
| Pendulum hardness according to DIN EN ISO 1522, König pendulum damping test (120 µm wet on glass) | 7 h | [s] | 82 | 82 |
|  | 3 d | [s] | 157 | 161 |
|  | 2 d | [s] | 169 | 176 |
|  | 3 d | [s] | — | — |
|  | 7 d | [s] | 189 | 190 |
|  | Temperature | [° C.] | 23 | 23 |
|  | Humidity | [%] | 55 | 55 |
| Drying time Determination of the degree of drying of coatings according to DIN 53150 | Dust dry | [min.] | 14 | 14 |
|  | Tack-free | [h] | 2 | 2 |
|  | Dry to the touch | [h] | 5 | 5 |
|  | Temperature | [° C.] | 24.8 | 24.8 |
|  | Humidity | [%] | 72 | 72 |
| Scratch resistance according to DIN EN | 1 day | [0-5] good | 0 1 | 1 |

|  |  |  | Example 1 | Example 3 |
|---|---|---|---|---|
| ISO 20566 | 7 days | [0-5] poor | 1 | 1 |
| Resistance to fluids according to DIN EN ISO 2812-4 after 24 h | 1 min. acetone | [0-5] good | 0 5 | 5 |
|  | 1 min. BA/EA*) (1:1) | [0-5] poor | 5 4 | 4 |
| Resistance to fluids according to DIN EN ISO 2812-4 after 7 d | 1 min. acetone | [0-5] good | 0 5 | 5 |
|  | 1 min. BA/EA*) (1:1) | [0-5] poor | 5 4 | 4 |

*)BA/EA: butyl acetate/ethyl acetate

The invention claimed is:

1. A method for producing polyisocyanates comprising urethane groups and having APHA colour indices <50 Hazen comprising reacting di- to tetra-valent organic polyhydroxy compounds with excess amounts of toluylene diisocyanate and then removing unreacted excess toluylene diisocyanate to residual contents <0.5 wt. % by distillation, wherein the toluylene diisocyanate has a content of 2-chloro-6-isocyanato-methylcyclohexadienes <5 wt·ppm.

2. The method according to claim 1, wherein the toluylene diisocyanate is produced by gas phase phosgenation.

3. The method according to claim 1, wherein the toluylene diisocyanate has a content of 2-chloro-6-isocyanato-methylcyclohexadienes below the detection limit of 1 wt·ppm.

4. The method according to claim 1, wherein the polyisocyanates comprising urethane groups have APHA colour indices <30 Hazen.

5. The method according to claim 1, wherein the toluylene diisocyanate is 2,4-toluylene diisocyanate or a mixture thereof with up to 35 wt. %, based on the mixture, of 2,6-toluylene diisocyanate.

6. The method according to claim 1, wherein the polyhydroxy compounds are di- to tetra-hydric alcohols having a molecular weight of from 62 to 146 and/or polyether polyols having a molecular weight in the range of from 106 to 600 prepared therefrom by addition of ethylene oxide and/or propylene oxide.

7. The method according to claim 1, wherein the polyhydroxy compounds are a mixture of trimethylolpropane and diethylene glycol.

8. A polyisocyanate comprising urethane groups produced by the method according to claim 1.

9. A method comprising utilizing the polyisocyanates comprising urethane groups according to claim 8 as the polyisocyanate component in a polyurethane coating.

10. The method according to claim 9 wherein the polyisocyanates comprising urethane groups is a crosslinker in two-component polyurethane coatings.

11. A polyurethane adhesives comprising the polyisocyanate produced by the method according to claim 8.

* * * * *